United States Patent [19]

Syers

[11] Patent Number: 5,511,565
[45] Date of Patent: *Apr. 30, 1996

[54] GUIDED BONE AND TISSUE GENERATION DEVICE AND METHOD TO BE USED DURING OR AFTER DENTAL SURGERY OR JAW SURGERY

[76] Inventor: Charles S. Syers, 325 Ascot Rd., Hillsborough, Calif. 94010

[*] Notice: The term of this patent shall not extend beyond the expiration date of Pat. No. 5,297,563.

[21] Appl. No.: 213,491

[22] Filed: Mar. 15, 1994

Related U.S. Application Data

[63] Continuation-in-part of Ser. No. 862,894, Apr. 3, 1992, Pat. No. 5,297,563.

[51] Int. Cl.$^6$ ..................................... A61B 19/00
[52] U.S. Cl. ..................... 128/898; 128/859; 433/229
[58] Field of Search ..................... 128/897–898, 128/859, 861; 433/215, 229; 606/60, 72–75, 86

[56] References Cited

U.S. PATENT DOCUMENTS

| | | | |
|---|---|---|---|
| 4,533,326 | 8/1985 | Anthony | 433/229 |
| 5,059,123 | 10/1991 | Jernberg | 433/229 |
| 5,297,563 | 3/1994 | Syers | 433/229 |

*Primary Examiner*—Angela D. Sykes
*Assistant Examiner*—John P. Lacyk
*Attorney, Agent, or Firm*—Townsend and Townsend and Crew

[57] ABSTRACT

The invention relates generally to methods and devices for facilitation of guided tissue and bone regeneration after occurrence of a bony deficit. A mechanical barrier dimensioned to cover the deficit and means for securing the barrier in place are described. More specifically, devices and methods for use in conjunction with tooth extraction are described.

15 Claims, 3 Drawing Sheets

GUIDED BONE AND TISSUE GENERATION DEVICE AND METHOD TO BE USED DURING OR AFTER DENTAL SURGERY OR JAW SURGERY

CROSS-REFERENCE TO RELATED APPLICATION

This application is a continuation-in-part application of U.S. Ser. No. 07/862,894, filed Apr. 3, 1992 now U.S. Pat. No. 5,297,563.

BACKGROUND OF THE INVENTION

The invention relates generally to devices and methods to promote guided bone and tissue healing after occurrence of an inflammatory, traumatic or surgical wound. More specifically, the invention relates to the guided healing of a bony deficit of the maxillae or mandible after extraction of an impacted molar tooth, after periodontal surgery, or after fracture repair or jaw surgery for any reason.

Normally, when a patient's wisdom tooth or molar is removed or when a surgery is performed, a surgeon incises a flap of soft tissue in back of, or posterior to, an adjacent tooth to visualize the impacted tooth or surgical field. This operation is routine. Sometimes the bone in the field is absent or unhealthy. This problem may be present before the operation or after the surgery is completed. For example, pre-operatively the bone may have begun a resorptive process due to inflammation, swelling or other injury or deficit in the vicinity of an impacted third molar.

The oral surgeon attempts to suture the incised tissue flap back together, creating an environment for bone healing. If the bone does not heal properly and regenerate, then the patient may develop a periodontal pocket or an open space associated with the surgical area. Because this area tends to retain trapped food or become infected, it rarely heals well. Poor bone healing in this circumstance is more prevalent in the older population, but can also occur in young patients.

To encourage maximum healing, i.e., up to the bone's proper level, one factor is the need to protect the proper environment required by the precursor bone cells, called progenitor cells, to form new bone. These multipotential bone cells which form new bone are undifferentiated and demand a specific type of biological medium to form mature bone. This process may take about one or two months. When a surgeon closes a wound, the epithelium in that wound invaginates or creeps into the field that has been created by removing the tooth or performing surgery. The invagination process is very fast, usually taking 7–14 days. Once invagination of epithelium occurs, it is impossible for the progenitor bone cells to occupy this location to create new bone. Thus, the bone healing is compromised, and the potential level of bone growth is not achieved.

SUMMARY OF THE INVENTION

The invention provides a mechanical and biological barrier and means for securing the barrier in position. The barrier is placed over a tissue deficit, such as a bony deficit, to provide a shaped coverage. Thus, the bony deficit is protected from epithelial invagination until progenitor cells allow bone to regenerate. The barrier may be formed of a resorbable material; alternatively, it can be nonresorbable and require subsequent surgical removal.

Once positioned, the barrier is secured or anchored into place by any suitable means. Examples of means for securing the barrier include suture material, screws, staples, tacks, clips and pincers. Generally, after the means for securing the barrier are placed, the edges of the tissue or flap adjacent to the wound are brought closer together and secured. Thus, a barrier is formed between the overlying soft tissue and underlying bony surgical field or defect.

A structure in the vicinity of the bony defect can be used to stabilize or position the barrier or the means for securing the barrier. For instance, a natural structure, such as a tooth or bone, can receive a harness which is secured to the barrier or the soft tissue. Additionally, a non-natural structure, such as an implant, a dental appliance, or an orthopedic device, can be used instead of a natural structure.

An elongate member, such as a cord, filament or tab, can be attached to the barrier to facilitate removal of the barrier by providing a convenient grasping point for the surgeon or practitioner. The elongate member is usually placed partially within a hollow structure, such as a tube or cylinder. The hollow structure is dimensioned to accept the barrier. Thus, when traction is placed on the elongate member while the hollow structure is stabilized, the barrier is pulled into the hollow structure.

Finally, the under surface of the barrier may contain a support foot or support ridge to elevate its position from the field or defect. This allows more bone regeneration. The foot or ridge can be modified.

BRIEF DESCRIPTION OF THE FIGURES

FIG. 3A is a side view and FIG. 3B is a top view.

DETAILED DESCRIPTION OF A PREFERRED EMBODIMENT

The invention provides methods and devices to facilitate tissue guided regeneration of a bony deficit. The bony deficit may have occurred from a surgical procedure, such as extraction of an impacted molar, or from other causes such as trauma, a tumor or inflammatory disease.

The barrier of the invention acts as a discrete member to prevent epithelial regeneration into an area where grafted bone or bone filler has been placed or compacted. In addition, barriers of the invention can include fasteners so that the barrier can be placed in a specific anatomical location which may be inaccessible to conventional techniques for suturing.

A mechanical barrier of the invention is shapeable to allow the user to adapt the size or shape of the barrier as appropriate to cover a bony deficit. For instance, the barrier can be cut, folded, or otherwise adapted to a specific bony deficit of interest. The barrier is placed beneath the periosteum, which is a specialized connective soft tissue covering of bone. Typically, a portion of the barrier, such as the edges, is placed beneath the periosteum and the remainder of the barrier is external to the periosteum and thus forms an outer surface covering the bony defect.

Figure 1:
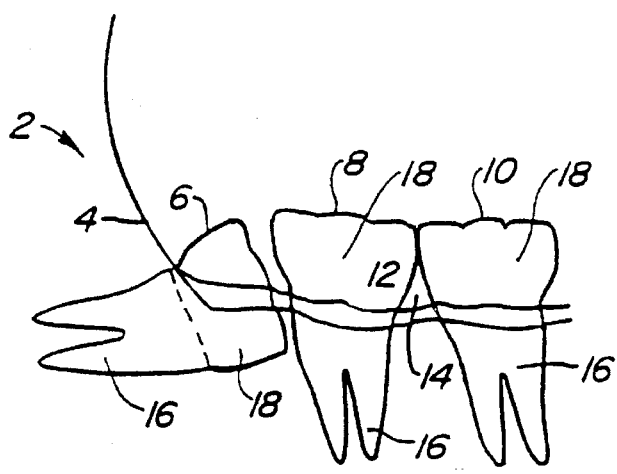
FIG. 1 is a schematic of molars and an impacted wisdom tooth.

Referring to FIG. 1, a schematic of a mandible 2, an impacted wisdom tooth 6, a second molar 8 and a first molar 10 are shown. A root 16 and a crown 18 are components of each tooth. Wisdom tooth 6 is posterior or dorsal to molar 8 as indicated by the direction of arrow 20. An anterior or ventral direction is indicated by the direction of arrow 22. A normal bone line 4 and a normal gum line 12 are depicted. Wisdom tooth 6, being impacted, is not normally erupted. It is locked into position by bone or, in some cases, by a surface of adjacent molar 8.

Figure 2:
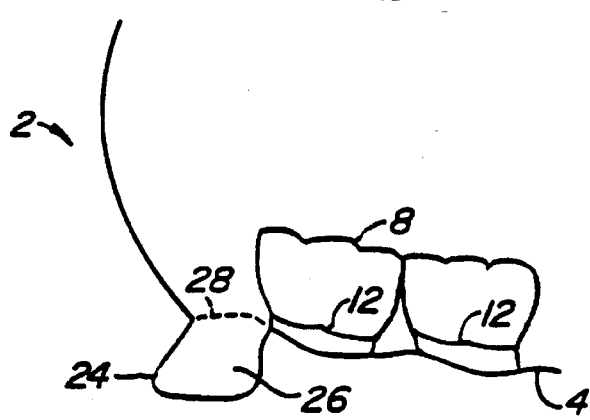
FIG. 2 is a schematic showing a bony deficit after removal of an impacted wisdom tooth.

After surgical removal of wisdom tooth 6, a bony deficit 26 is left in mandible 2 as shown in FIG. 2. An abnormal bone line 24 is evident. An incised portion of mucosal tissue 28 may partially cover deficit 26. A mechanical barrier 36 of dimensions appropriate to cover deficit 26 is placed over deficit 26. Barrier 36 is a flexible shapeable membrane. Placement of barrier 36 typically occurs contemporaneously with the surgical procedure responsible for surgical removal of wisdom tooth 6, but may occur at another time in some cases. The patient might be under general anesthesia or sedation during the procedure, but a local anesthetic is also appropriate. After it is properly positioned, barrier 36 is secured in place.

The dimensions of barrier 36 vary with the clinical requirements. In general, the dimensions are sufficient to allow coverage of a bony deficit of interest. Barrier 36 is preferably formed of a resorbable material. Examples include biodegradable ceramics, modified starches or gelatins, polyamides, and resorbable polymers such as polymers of glycolic or lactic acid. Alternatively, barrier 36 could be formed of a nonresorbable material such as polytetrafluoroethylene, or PTFE or expanded PTFE, which is marketed under the tradename GORE-TEX™. Other fluoroplastics or fibrous fabric materials could also be used. Additionally, barrier 36 may be made of a cellulose membrane filter such as MILLIPORE™. Application of galvanic current to the barrier is facilitated by the incorporation of conductive fibers into the barrier or the fasteners. Such conductive fibers can be formed of metal or an alloy, for example.

Figure 3A:
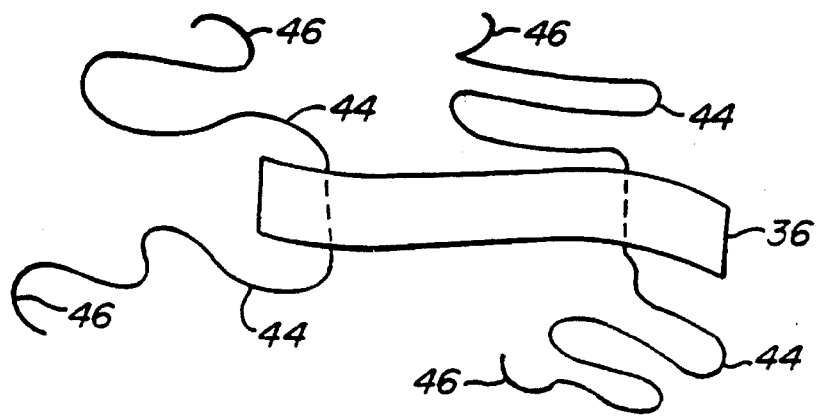
FIGS. 3A–B define a device constructed in accordance with the invention showing a barrier with anchoring sutures.
Figure 3B:
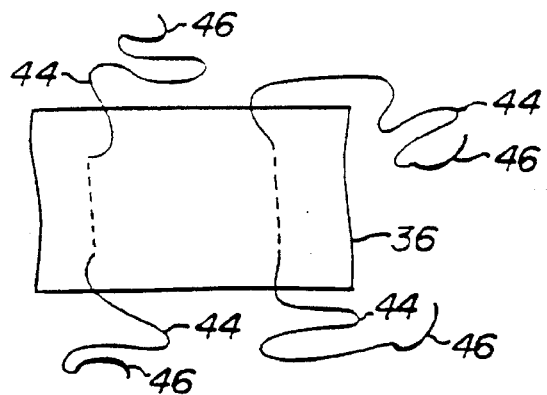

Barrier 36 is secured into position by any of a number of means. For example, barrier 36 may be stitched in place with suture which is either resorbable or nonresorbable, single filament or multi-filament. Suture materials and needles are well known in the art. FIG. 3A is a side view of barrier 36. Suture material 44 is swaged or placed through two locations of barrier 36, preferably near two ends. Each suture 44 is supplied with a pair of swaged or fused-on needles 46. A top view of barrier 36 with suture material 44 and needles 46 is sketched in FIG. 3B.

Suture material with a swaged-on needle is useful to anchor the barrier through the soft tissue. Preferably, two or more sutures with attached needles are provided allowing each needle to pierce its respective overlying portion of the soft tissue flap.

Other arrangements of sutures 44 and needles 46 are apparent; for instance, the numbers and location could vary. Needle 46 may be provided separately from suture 44 instead of being swaged or a single needle 46 may be used instead of pairs.

Alternative means of securing the barrier include a pincers arrangement. The pincers may be a clamp-like device which grasps a natural structure in the vicinity of the deficit, such as a molar tooth. Alternatively, the pincers may include a harness or bracket which engages a nearby nonnatural structure, such as an orthodontic bracket, wire, implant or orthopedic appliance. The pincer can be reinforced with suture material or other means to secure its location, or it can be spring loaded to prevent its dislodgement.

In one configuration, the pincers are a clamp-like device which grasps a nearby tooth and fits around the back of the tooth and are attached to the barrier, usually at an edge. The pincers may be opened and applied with a special device. Another form of pincers are anchored with sutures which tie into the wound or around an adjacent tooth, usually a second molar. The pincers can wrap around a dental appliance or other non-natural structure instead of a tooth, which acts as an anchoring device.

The pincers are preferably made of polyvinyl although metal can be used instead. Alternatively, the pincers could be formed of a resorbable material, such as a polysaccharide, having an inherent resilience or springiness.

Figure 4A:
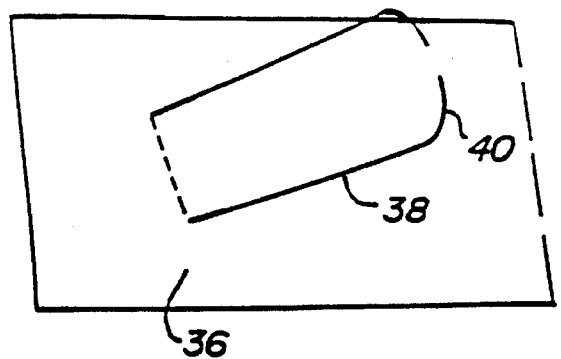
FIG. 4A defines a device constructed in accordance with the invention showing a barrier with pincers-clamp anchor.

A simplified pincer 38 is shown in FIG. 4A. A terminal portion of pincer 38 is bent or crimped to form arms 40 which engage a tooth to secure barrier 36. Arms 40 are placed around a tooth at an interproximal space 14.

Figure 4B:
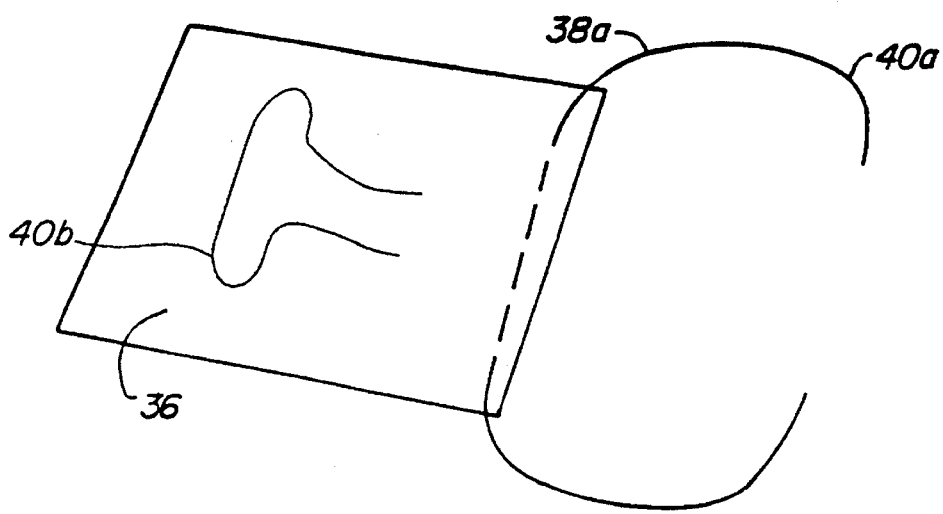
FIG. 4B defines a device constructed in accordance with the invention showing a support foot or ridge.

A support foot or ridge can be included. See FIG. 4B. In this embodiment, the previously described pincers are modified to act as a support foot to elevate barrier 36 from the bony defect. In addition, a support foot 40b is attached to the central portion of the barrier. Movable extension 38a terminates in foot 40a. By positioning at least one of foot 40a or 40b on or around a structure in the vicinity of the bony defect, barrier 36 is held above the defect.

In use, barrier 36 is slipped into the wound to cover bony defect 26. If using suture 44 to secure barrier 36, needle 46 is brought underneath flap 28 and pushed outward through the flap tissue. Each needle 46 pierces its respective portion of flap 28. When suture 44 is tied together, the edges of flap 28 are approximated. Barrier 36 is interposed between overlying soft tissue and underlying bony tissue. The edges of the barrier can be cut, shaped and adapted to the underlying area.

If flap 28 has insufficient tissue to stitch, or at the discretion of the surgeon, suture 44 is alternatively wrapped around molar 8, brought to interproximal region 14, tied off and held in this position. Additional sutures are placed to stabilize this position. If barrier 36 is formed of a nonresorbable material, then barrier 36 is surgically removed after sufficient bony regeneration has occurred.

Figure 5:
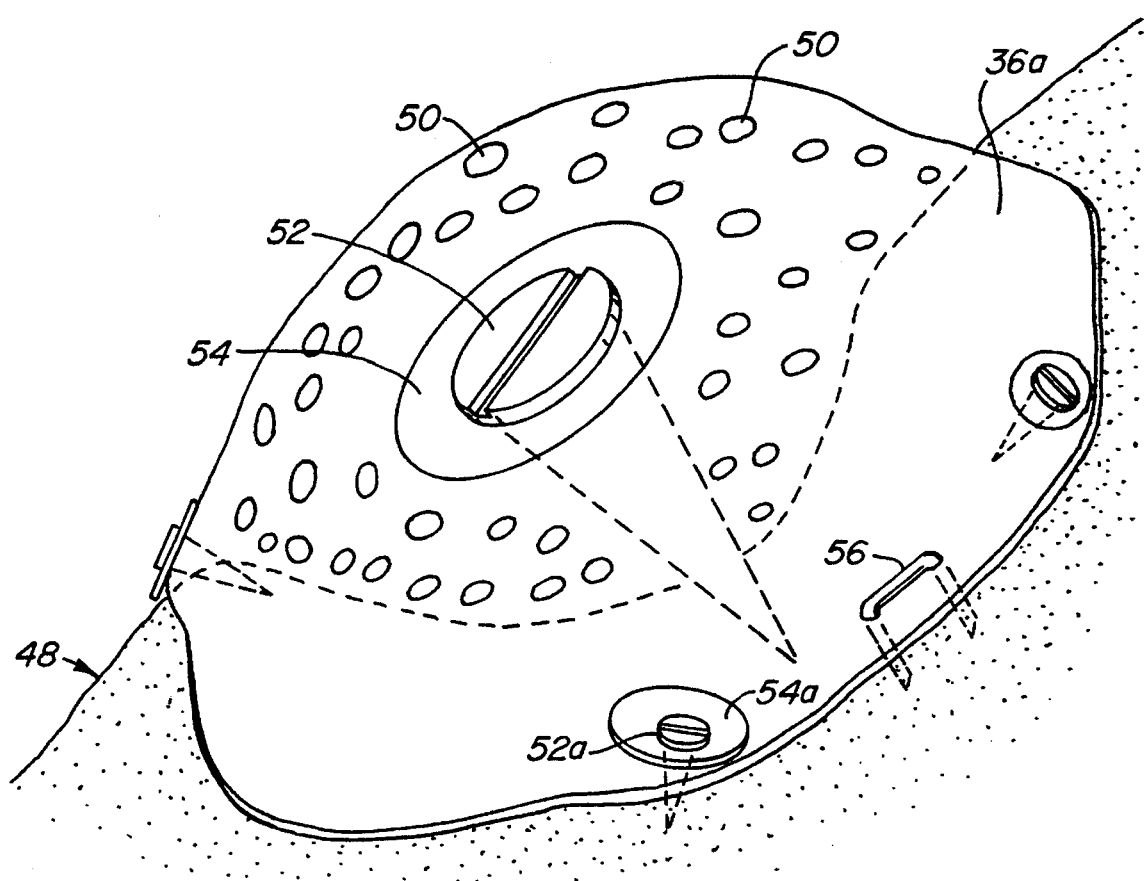
FIG. 5 defines a device constructed in accordance with the invention showing an embodiment including screws for fastening the barrier and a central support.

The device of the invention is intended for placement beneath periosteum, and a modification of the invention is shown in position in FIG. 5. Bone line 48 is abnormally receded or excavated in an area subsequently packed with bone filler 50 and covered with barrier 36a. This embodiment uses two types of fasteners. One fastener is a simple headed screw 52/52a with a flange or washer-like collar 54/54a which contacts the barrier 36a. The flange is typically provided with an opening, such as a hole, to receive the screw. The screws can be adapted for size as shown by a large central anchoring screw 52 and smaller peripheral screws 52a securing the edges of barrier 36a. The screw can also function as a foot for support.

In addition to the screws, a staple 56 is used in this embodiment to further secure the barrier 36a. The secured barrier creates a tent which covers the grafted bone or substitute bone material 58. Any of the fasteners or means for securing the barrier can be formed of nonresorbable materials, such as plastics, metals and alloys. Alternatively, they can be formed of resorbable materials, such as the materials described for the barrier.

Figure 6:
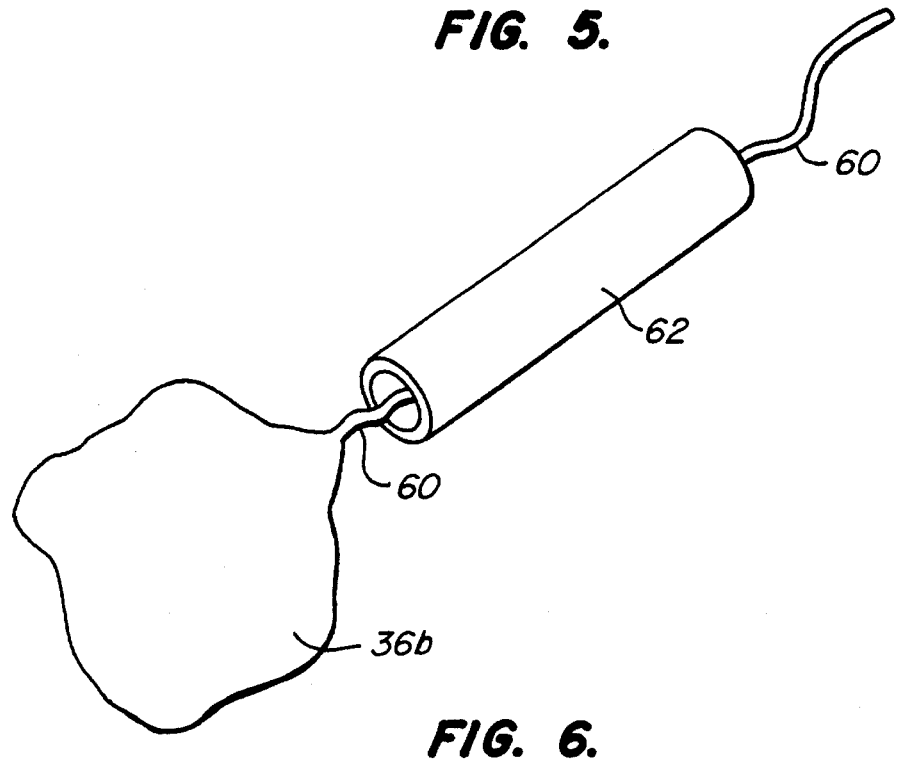
FIG. 6 defines a device constructed in accordance with the invention showing a pull-tube and a pull-wire for facilitation of removal of the barrier.

A pull-out tube 62 and pull-out cord 60 can be added to a barrier 36b to facilitate removal of the barrier. See FIG. 6. This feature is especially useful in embodiments having a nonresorbable barrier 36b in combination with resorbable fasteners. Cord 60 is an elongate member which is preferably flexible. It is attached to barrier 36b and facilitates removal of the barrier by providing a convenient grasping point for the surgeon. Tube 62 is a hollow body dimensioned to accept the cord and, subsequently, the barrier as the barrier is pulled through tube 62. While presented as a cylinder in this embodiment, tube 62 may take any convenient shape. Cord 60 and tube 62 can be formed of any suitable material. Preferably, the material is nonresorbable.

Bone substitute materials, which are known in the art, may be used in conjunction with this invention. Some examples of these materials are hydroxyapatite, powdered bone, calcium carbonate, freeze-dried bone, autologous bone, and various types of grafts. These materials may be placed into the deficit or socket area. For example, if the surgeon were treating a periodontal defect, the diseased area could be debrided and grafted with natural bone material, usually taken from the patient. The barrier is placed on top of the graft to protect it. Alternatively, another bone substitute material is placed into the deficit instead of a natural graft. In either case, the deficit can be partially or completely filled with the selected material.

Further, the barrier is useful to protect a blood clot which forms after a surgical procedure. By protecting this blood clot, i.e., by covering the clot, the barrier helps prevent a condition called osteitis, commonly called "dry socket." Dry socket is painful, and it occurs when the blood clot becomes gelatinous and lyses in the open wound. After clot lysis, the bone is exposed to bacterial invasion from the oral cavity. The invention facilitates prevention of poor healing that causes advancing periodontal disease, gum disease, tissue dehiscence or loss of bone, especially after a third molar is removed or in conjunction with orthognathic surgery, periodontal surgery, or jaw surgery.

The invention is preferably packaged in sterile kits including the barrier and an anchoring means. As discussed, the anchoring means may be any of a number of arrangements such as suture material, typically including a swaged-on needle, a pincer arrangement, screws, staples, tacks or other fasteners. Additionally, a kit may provide a barrier having one type of anchoring means at one end and another type of anchor at its other end. After deciding which type of anchor to use, the surgeon simply snips off and discards the undesired anchor. In some cases, more than one type fastener on a single barrier membrane can be used due to special anatomical or access considerations.

Although it is contemplated that the invention will find most application in third molar areas, the invention and its modifications can be otherwise utilized. For example, the device and method can cover edentulous or tooth-bearing ridges in an attempt to maintain levels of bone or in an attempt to regraft levels of bone. Additionally, the invention is useful in other medical settings, such as in orthopedic surgery. The attachment or securing systems can be made larger or smaller, as indicated. Sutures or other anchoring means can be placed at both ends or other locations of the barrier to protect grafts of long bones, wrist and ankle bones, hip grafts, cervical grafts and other orthopedic procedures associated with bone deficits.

The foregoing is offered primarily for purposes of illustration. It will be readily apparent to those of ordinary skill in the art that the operating conditions, materials, procedural steps and other parameters of the system described herein may be further modified or substituted in various ways without departing from the spirit and scope of the invention. For example, pins or tacks could be used to secure the barrier in place although screws, sutures and pincers have been detailed. Thus, the invention is not limited by the preceding description, but rather by the appended claims.

What is claimed is:

1. A method to facilitate tissue guided regeneration of a bony deficit of a bone using a mechanical barrier sized to cover said deficit comprising:
   a. placing the barrier over the deficit and beneath the periosteum of the bone;
   b. shaping the barrier to the deficit; and
   c. securing the barrier in place by applying a member of the group consisting of a screw and a staple.

2. The method of claim 1 wherein step (b) comprises cutting the barrier.

3. The method of claim 1 wherein step (c) comprises applying a screw through the barrier and into the bone.

4. The method of claim 3 wherein step (c) further comprises contacting a flange to the barrier and applying the screw through the flange.

5. The method of claim 1 further comprising:
   a. allowing bony regeneration at the site of the deficit; and
   b. removing the barrier after bony regeneration has occurred.

6. The method of claim 5 further comprising a step of selecting a barrier which is attached to a cord adapted to facilitate removing the barrier.

7. The method of claim 6 further comprising a step of establishing placement of the cord within a tube dimensioned to accept the barrier.

8. The method of claim 1 further comprising a step of filling at least a portion of the deficit with a member of the group consisting of natural bone tissue and bone substitute material.

9. A method of tissue guided regeneration to prevent osteitis of a bony deficit after a surgical procedure resulting in a blood clot on a bone surface using a mechanical barrier dimensioned to cover the clot on the bone surface comprising:
   a. placing the barrier on the clot;
   b. positioning the barrier beneath the periosteum of the bone;
   c. shaping the barrier to the deficit; and
   d. securing the barrier in place.

10. The method of claim 9 wherein step (d) comprises applying a member selected from the group consisting of a screw and a staple.

11. A kit for promotion of guided healing of a bony deficit comprising:
   a. a shapable mechanical barrier dimensioned to overlay the deficit further including a cord attached to said barrier;
   b. a means for securing the barrier in place; and
   c. a tube dimensioned to accept the cord therethrough.

12. The kit of claim 11 wherein the securing means comprises a member selected from the group consisting of a suture, a screw, a staple, a tack, and a clip.

13. The kit of claim 11 wherein the securing means comprises a harness adapted to engage a natural or non-natural structure in a vicinity of the deficit.

14. The kit of claim 11 wherein the securing means is attached to the barrier.

15. The kit of claim 11 wherein the barrier is conductive of galvanic current.

* * * * *